(12) United States Patent
Rimlinger et al.

(10) Patent No.: US 7,241,277 B2
(45) Date of Patent: Jul. 10, 2007

(54) SECURITY DEVICE FOR A SYRINGE (75) Inventors: Thierry Rimlinger, L'Isle d'Abeau (FR); Michel Pouget, Domarin (FR); Philippe Dodier, Sainte-Foy-les-Lyon (FR)

(73) Assignee: Compagnie Plastic Omnium, Lyons (FR)

( * ) Notice: Subject to any disclaimer, the term of this patent is extended or adjusted under 35 U.S.C. 154(b) by 233 days.

(21) Appl. No.: 10/491,714

(22) PCT Filed: Oct. 15, 2002

(86) PCT No.: PCT/FR02/03531

§ 371 (c)(1),
(2), (4) Date: Apr. 5, 2004

(87) PCT Pub. No.: WO03/033060

PCT Pub. Date: Apr. 24, 2003

(65) Prior Publication Data

US 2004/0267206 A1 Dec. 30, 2004

(30) Foreign Application Priority Data

Oct. 15, 2001 (FR) .................................. 01 13255

(51) Int. Cl.
*A61M 5/32* (2006.01)
*A61M 5/20* (2006.01)
*A61M 5/00* (2006.01)
*A61M 5/178* (2006.01)

(52) U.S. Cl. ...................... 604/198; 604/110; 604/156; 604/162; 604/163; 604/164.08; 604/187; 604/192; 604/197; 604/263

(58) Field of Classification Search ................ 604/110, 604/111, 156, 162, 163, 164.08, 187, 192, 604/195, 196, 197, 198, 263
See application file for complete search history.

(56) References Cited

U.S. PATENT DOCUMENTS 4,950,250 A * 8/1990 Haber et al. ................ 604/192

(Continued)

FOREIGN PATENT DOCUMENTS

DE        38 43 839 A1    7/1989

(Continued)

*Primary Examiner*—Tatyana Zalukaeva
*Assistant Examiner*—Michael Bogart
(74) *Attorney, Agent, or Firm*—Oliff & Berridge, PLC (57) ABSTRACT

The present invention relates to a safety device (2) for a prefilled syringe (1), the syringe comprising a body (3), a needle carrier (4), a piston (6) movable inside the body, and a piston rod (7) suitable for pushing the piston inside the body towards the needle carrier. The device comprises a protective sheath (10) in which the syringe body can slide between an injection position and a safe position in which the needle is withdrawn inside the sheath, said device (2) comprising a resilient element (15) suitable for acting on the syringe to bring in into its safe position after injection, said resilient element presenting two axial ends and comprising at least two elastically-deformable arms extending between said two axial ends, one of the ends (20) being arranged so as to be capable of sliding freely relative to the piston rod (7) prior to injection, and/or one of the ends being arranged in such a manner as to be capable of being fixed to the protective sheath (10) in a position of adjustable height.

22 Claims, 5 Drawing Sheets

U.S. PATENT DOCUMENTS

| | | | |
|---|---|---|---|
| 5,053,017 A * | 10/1991 | Chamuel | 604/192 |
| 5,114,409 A * | 5/1992 | Kole et al. | 604/192 |
| 5,246,427 A * | 9/1993 | Sturman et al. | 604/192 |
| 5,256,152 A * | 10/1993 | Marks | 604/198 |
| 5,295,972 A * | 3/1994 | Mischenko | 604/192 |
| 5,738,660 A * | 4/1998 | Luther | 604/164.08 |
| 6,409,706 B1 * | 6/2002 | Loy | 604/198 |
| 6,613,022 B1 * | 9/2003 | Doyle | 604/192 |
| 6,616,638 B2 * | 9/2003 | Peters, III | 604/192 |
| 6,719,731 B2 * | 4/2004 | Parmigiani | 604/192 |
| 6,942,652 B1 * | 9/2005 | Pressly et al. | 604/508 |
| 6,986,759 B1 * | 1/2006 | Jeremijevic | 604/198 |

FOREIGN PATENT DOCUMENTS

| | | |
|---|---|---|
| EP | 0 317 518 A1 | 5/1989 |
| FR | 2 788 986 A3 | 8/2000 |
| FR | 2 815 545 A3 | 4/2002 |
| WO | WO 89/04681 | 6/1989 |
| WO | WO 01/85239 A2 | 11/2001 |

* cited by examiner

FIG_5  FIG_6

FIG_8    FIG_9

SECURITY DEVICE FOR A SYRINGE

The invention relates to a safety device for a syringe, in particular a prefilled syringe, the device comprising a protective sheath suitable for protecting the needle of the syringe after it has been used.

BACKGROUND OF THE INVENTION

European patent EP 0 317 518 discloses a device for protecting a syringe needle, which device comprises a protective case and a resilient ring having two diametrically-opposite coaxial extensions, one of the extensions forming an integral portion of one end of the protective case, and the other extension forming an integral portion of a nut connected to one end of the body of the syringe. The structure of that prior protective device is suitable for only one type of syringe, and the device is relatively complex to put into place on the syringe.

OBJECTS AND SUMMARY OF THE INVENTIONS

There exists a need for a reliable safety device, in particular one that is adapted to various types of syringe, that makes it possible to reduce the risks of accidental contamination as much as possible.

There also exists a need to have such a safety device presenting a structure that is relatively simple and that can be put into place easily on a syringe.

The invention provides a safety device for a prefilled syringe, the syringe comprising a body, a needle carrier at one end of the body, a piston movable inside the body, and a piston rod projecting beyond the body at its end opposite from the needle carrier and suitable for pushing the piston inside the body towards the needle carrier, said device comprising a protective sheath in which the syringe body can slide between an injection position in which the syringe needle extends outside the protective sheath, and a safe position in which the needle is withdrawn inside the protective sheath, the device comprising a resilient element suitable for acting on the syringe to bring in into its safe position after injection, said resilient element having two axial ends and at least two elastically-deformable arms extending between said two axial ends, one of the ends being arranged in such a manner as to be capable of sliding freely along the piston rod prior to injection, and/or one of the ends being arranged so as to be capable of being fixed to the protective sheath in a position of adjustable height.

The invention is particularly well adapted to prefilled syringes, and in particular to syringes for single use.

By means of the invention, the elastically-deformable arms are not prestressed prior to use of the syringe, either because the resilient arms are in their rest state, after the resilient element has been put into place on the piston rod, given that one of the ends of the resilient element is free, or else because the distance between the two axial ends of the resilient element is adapted to the dimensions of the syringe by means of the above-mentioned adjustment.

Thus, the elastically-deformable arms retain their resilient return ability, even after the safety device has been stored for a long period of time and after the content of the syringe has been injected. The arms are thus capable of exerting sufficient resilient force to bring the syringe body into the safe position in which the needle is withdrawn inside the protective sheath.

Furthermore, when one of the axial ends of the resilient element is arranged in such a manner as to be capable of sliding freely relative to the piston rod, the common length of the elastically-deformable arms may be selected in such a manner that the resilient element is capable of being adapted to different types of syringe, said length being shorter than the length of the piston rods of the various types of syringe. When one of the ends is arranged in such a manner as to be capable of being fixed to the protective sheath in a position of adjustable height, the adjustment can be adapted to the dimensions of the syringe that is to be protected. The safety device of the invention is suitable for various types of syringe, in particular 0.5 milliliter (ml) syringes and 1 ml syringes, thus making it possible to have only one type of safety device for an entire range of syringes.

In addition to the fact that it is suitable for a plurality of types of syringe, the safety device can also serve to protect syringes of a single type but for use with a variety of doses, i.e. the initial stroke of the piston can be adjusted depending on the dose of substance that is to be injected.

Finally, the resilient arms advantageously replace a helical spring, for example, thus making it possible to have a small number of component parts and to reduce the cost price of the safety device.

In a preferred embodiment of the invention, each of the elastically-deformable arms is defined by a strip of material, e.g. made of polypropylene (PP), sytrene butadiene sytrene (SBS), EBS, polyacrylate (PA), acetal resin (POM), or polyethylene (PE), this list not being limiting. The arms are preferably two in number and disposed facing each other.

The sheath can be made of a material that is transparent or semitransparent.

Each of the arms is advantageously generally V-shaped with its concave side facing inwards. This general V-shape enables good resilient return properties to be obtained for the arms.

In a preferred embodiment of the invention, the branches of the V-shape of each arm present different lengths, thereby further improving the resilient return properties of the arms.

These arms may locally present reduced width, enabling them to be splayed apart so that the resilient element does not impede insertion of the syringe into the protective sheath.

In a particular embodiment of the invention, the resilient element is made integrally with the protective sheath, thus making it possible to reduce the number of component parts for the safety device.

According to an aspect of the invention, one of the ends of the resilient element is connected to the protective sheath and its other end is put into place on the piston rod so as to be free to slide relative thereto, prior to injection.

The resilient element can then include an annular split ring at one axial end that is suitable for engaging on the piston rod and that can slide relative thereto.

The syringe can then be put simply and quickly into place in the safety device, in particular because the split ring can be engaged on the piston rod merely by applying pressure.

In a variant, the resilient element is constituted by a separate element suitable for being fitted to the protective sheath.

The resilient element may then include fixing straps each pierced by a plurality of orifices along a longitudinal direction of the strap, and the protective sheath may include portions in relief each associated with a strap, each portion in relief being capable of being fixed in one of the orifices in the associated strap. This makes it possible to adjust the height of the position where the straps are fixed to the protective sheath.

In addition, it is relatively easy to assemble the safety device and the syringe, with this merely requiring the syringe to be inserted into the sheath and then fixed to the straps thereof.

The end of the resilient element that is opposite from the straps may be secured to the piston rod of the syringe.

The device advantageously includes a holding element suitable for deforming from a position for holding the syringe body in the sheath to a disengaged position enabling the syringe body to slide freely relative to the sheath.

The holding element serves in particular to prevent the syringe body from moving in translation relative to the protective sheath while the needle is being introduced under the skin of the patient.

This holding element may comprise elastically-deformable tabs made in particular on the protective sheath and suitable for being splayed apart to take up the disengaged position.

In a particular embodiment of the invention, the resilient element comprises bridges of material connecting the elastically-deformable arms to said straps in such a manner that when the resilient element is subjected to compression, these bridges of material tend to splay the tabs apart.

In a variant, the resilient element includes an annular rib arranged to bear against said tabs and to move them apart when the elastic element is subjected to compression.

Thus, the holding element is disengaged after the piston rod has traveled along its injection stroke, thus avoiding any need for the user to perform any additional action for disengaging the holding element, other than those actions which are conventional when performing an injection.

The safety device may also include a locking element suitable for being fixed on the syringe body and arranged to retain it in its safe position after injection, said locking element possibly comprising teeth suitable for coming into abutment against a top edge of the protective sheath when the syringe body is in said safe position.

The safety device may include portions in relief suitable for preventing the syringe from turning relative to the protective sheath.

BRIEF DESCRIPTION OF THE DRAWINGS

The invention will be better understood on reading the following detailed description of non-limiting embodiments given with reference to the accompanying drawings, in which.

MORE DETAILED DESCRIPTION

Figure 1:
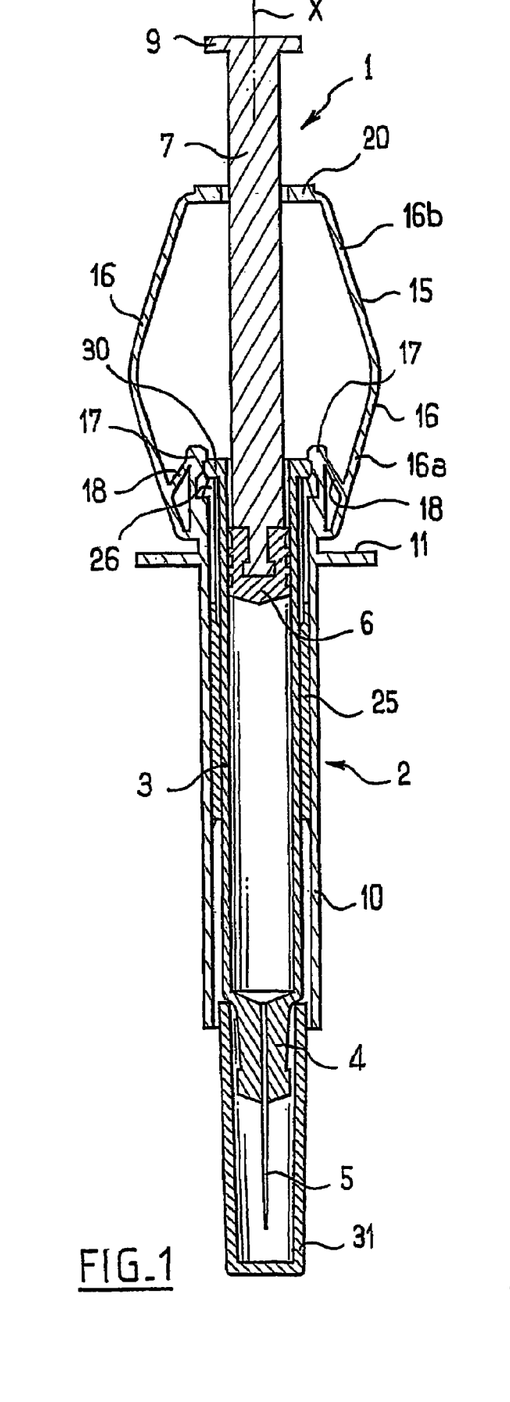
FIG. 1 is a diagrammatic and fragmentary axial section view of a syringe fitted with a safety device constituting a first embodiment of the invention, prior to use of the syringe.

FIG. 1 shows a single-use syringe 1 fitted with a safety device 2 in accordance with the invention.

In conventional manner, the syringe 1 comprises a body 3, a needle carrier 4 at one end of the body 3 and carrying a needle 5, a piston 6 that is movable in the body 3, and a piston rod 7 projecting from the body 3 at its end opposite from the needle carrier 4 and suitable for pushing the piston 6 into the body 3 towards the needle carrier 4. The rod 7 is terminated by a pusher 9 on which a user can exert pressure to inject the content of the syringe. The body 3 presents a collar 30 at its top end.

The safety device 2 comprises a protective sheath 10 that is circularly cylindrical about the axis X, having a collar 11 at its top end defining a bearing point for the fingers of a user performing an injection.

The safety device 2 also comprises a resilient element 15 comprising two elastically-deformable arms 16 each defined by a generally V-shaped strip of material with its concave side directed inwards, i.e. towards the axis X, and each facing the other.

The resilient element 15 is made integrally with the protective sheath 10.

In the example described, the lower branch 16a of the arm 16 is shorter than the upper branch 16b thus improving the resilient return capacity of the arm 16.

The protective sheath 10 has two elastically-deformable tabs 17 and its top end above the collar 11, each tab being connected to the bottom branch 16a of a corresponding arm 16 via a bridge of material 18.

Figure 2:
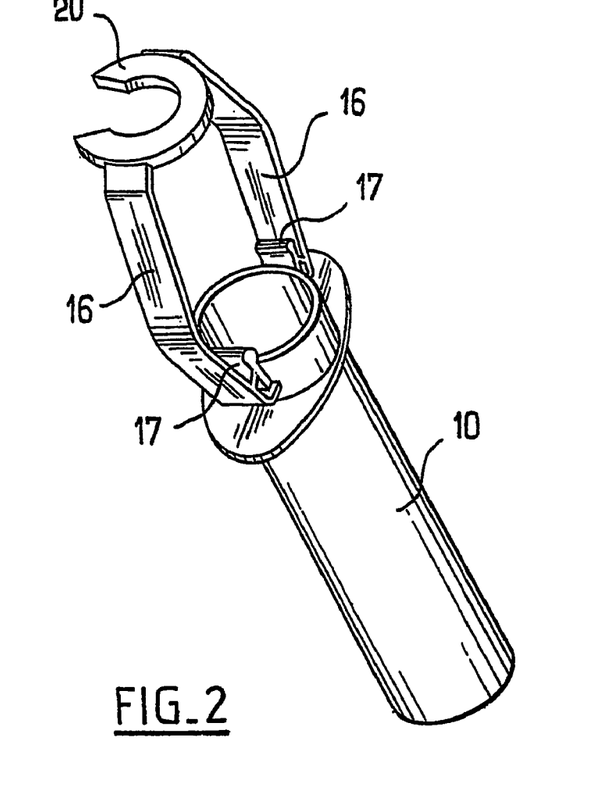
FIG. 2 is a diagrammatic and fragmentary perspective view of the protective sheath and the elastic element of the FIG. 1 device.

The arms 16 are connected together at their top ends by a split ring 20, as can be seen in FIG. 2 in particular. The split ring 20 is for engaging around the piston rod 7, the inside diameter of the ring 20 being greater than the section of the rod 7 so as to allow it to slide freely along the rod 7. The height of the arms 16 is selected to that the ring 20 remains below the pusher 9 on the rod 7, thus enabling the two arms 16 to avoid being prestressed prior to use of the syringe.

A sleeve 25 that is circularly cylindrical about the axis X is fixed around the syringe body 3. This sleeve 25, which is shown in isolation in FIG. 3, has a plurality of elastically-deformable tabs 27, there being four in the example shown, but it also being possible for there to be six, the top edges of the tabs defining an annular bead 26. The bottom portion of the sleeve 25 presents a plurality of teeth 28, there being three in the element described, each made on an elastically-deformable tab 29.

Figure 3:
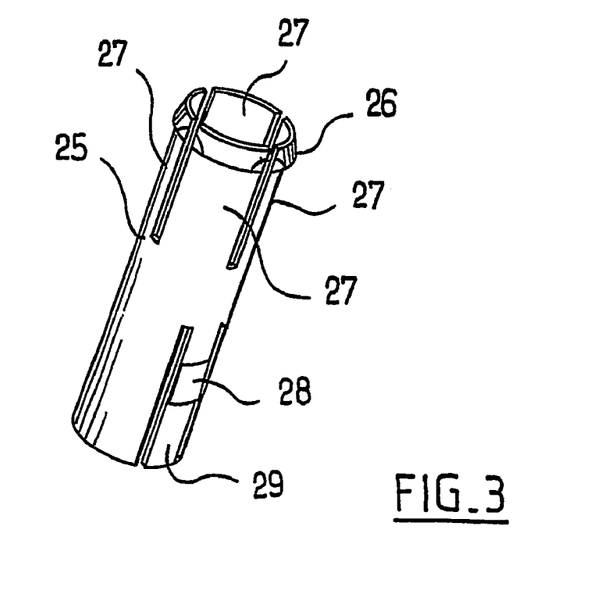
FIG. 3 is a diagrammatic perspective view of a sleeve of the safety device of FIG. 1 for receiving the syringe body.

The sleeve 25 remains secured to the syringe body 3 by friction and in particular forms a locking element in the meaning of the present invention, as explained below.

In addition, the elastically-deformable tabs 27 enable the sleeve 25 to receive syringe bodies of different diameters due to the small amount of spacing between the tabs.

When the sleeve 25 is in place within the protective sheath 10, the annular bead 26 bears against the top edge of the protective sheath 10. The collar 30 of the syringe rests against the bead 26 and is held thereagainst by means of the tabs 17. Thus, so long as the resilient element 15 is in its rest state, prior to injection and as shown in FIG. 1, the sleeve 25 and the syringe body 3 are prevented from moving in translation relative to the protective sheath 10.

Prior to use of the syringe, the needle 5 is advantageously protected by a cap 31.

The operation of the safety device 2 takes place as follows.

Firstly, the user causes the needle 5 to penetrate under the skin of the patient, the syringe then being prevented from moving in translation relative to the sheath 10, as specified above.

The user then pushes the pusher 9 so as to inject the content of the syringe. During this operation, the pusher 9 comes to bear against the annular ring 20 and causes the arms 16 to become compressed. The branches 16a then fold outwards so that the tabs 17 are splayed apart by the bridges of material 18, thus enabling the syringe body 3 to cease being held against the protective sheath 10.

At the end of its stroke, the piston 6 is held by friction in the syringe body 3 so that the piston rod 7 and the body 3 are secured to each other. When the user releases pressure on the pusher 9, the resilient return of the arms 16 acts, via thrust exerted by the ring 20 on the pusher 9, to cause the assembly constituted by the syringe 1 and the sleeve 25 to slide upwards relative to the protective sheath 10. At the end of this sliding, the needle 5 is fully withdrawn inside the protective sheath 10, in its safe position.

It should be observed that this sliding corresponds to reverse movement of the syringe in the protective sheath 10.

Figure 6:
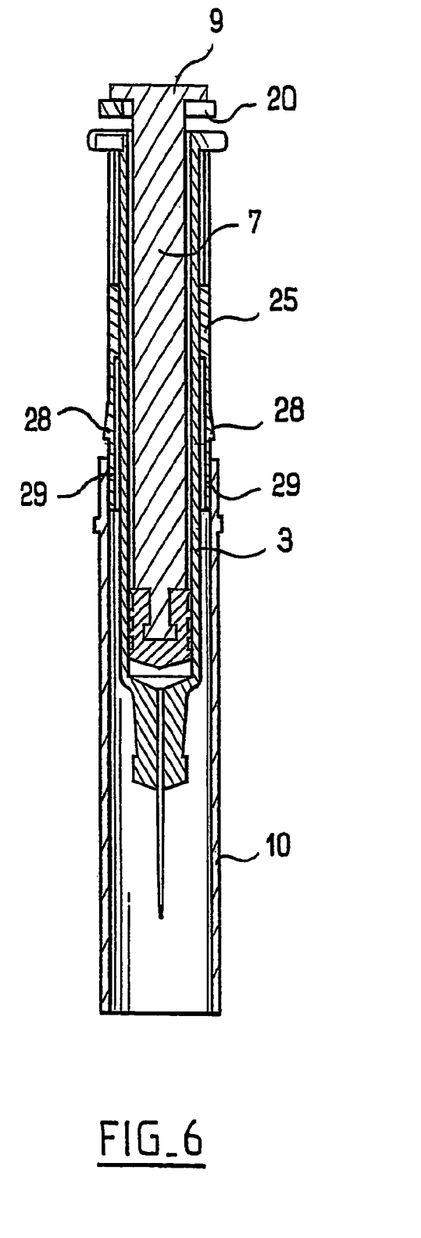
FIG. 6 is a diagrammatic section on VI—VI of the FIG. 5 device.

The teeth 28 of the sleeve 25 are then outside the protective sheath 10, and by resilient return of the tabs 29 in an outward direction, these teeth 28 can come into abutment against the top edge of the protective sheath 10 so as to prevent the assembly constituted by the sleeve 25 and the syringe 1 from sliding towards the protective sheath 10, as can be seen in FIG. 6. This causes the syringe 1 to be locked in this safe position relative to the protective sheath 10.

Figure 5:
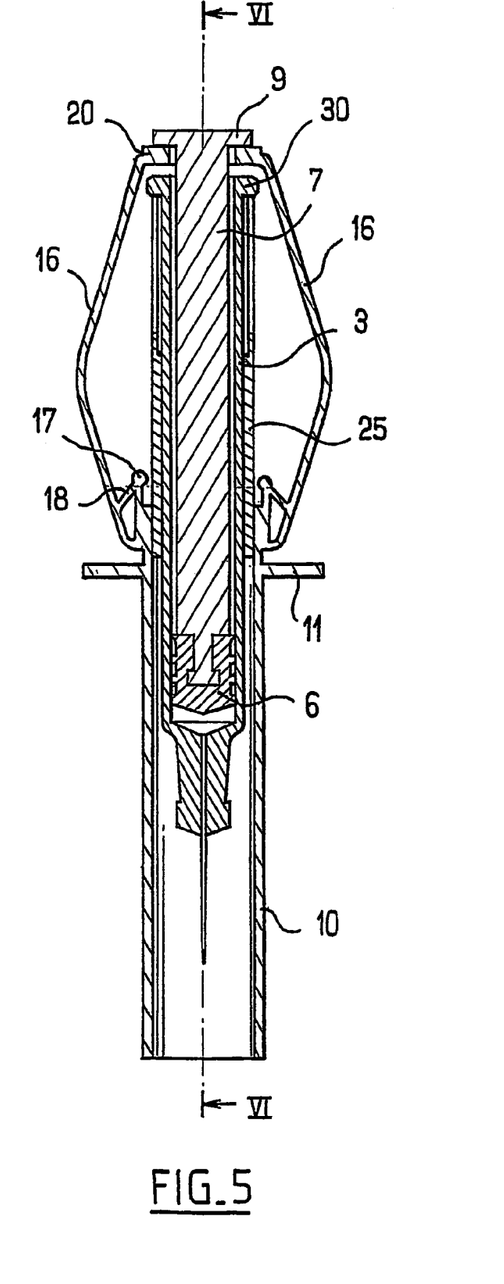
FIG. 5 is a view analogous to FIG. 1, after injection.

As can be seen in FIGS. 5 and 6, at the end of injection, the ring 20 presses against the pusher 9 about the collar 30.

Figure 4:
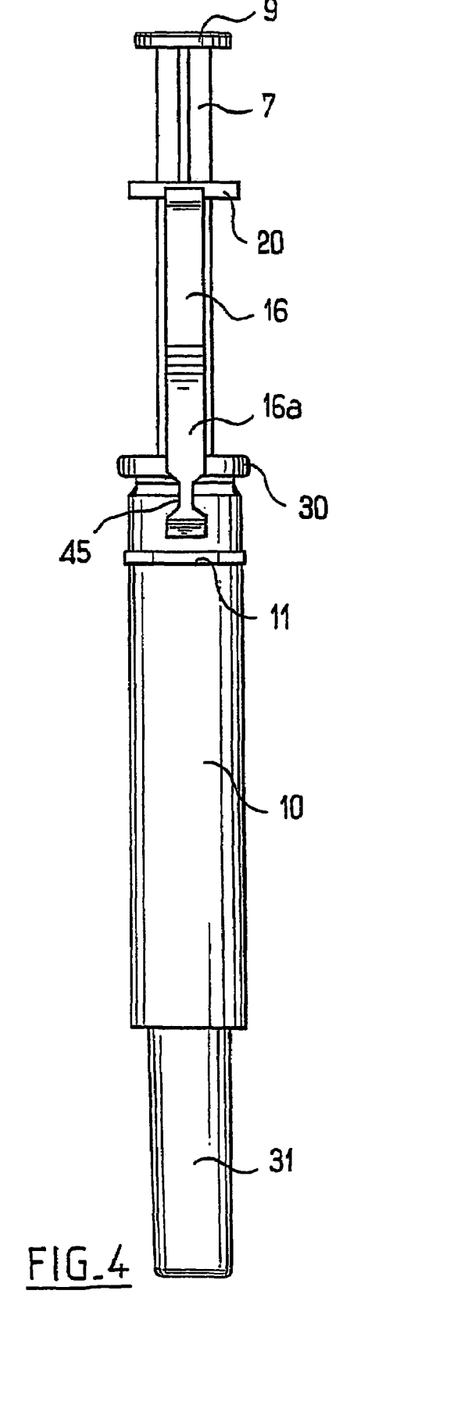
FIG. 4 is a side view of a variant of the FIG. 1 safety device.

The arms 16 have a local narrowing 25 enabling them to be spaced apart from the axis X so as to leave sufficient space for introducing the syringe 1 into the protective sheath 10, as can be seen in FIG. 4.

The tabs 17 may be spaced apart by elements other than the bridges of material 18.

Figure 7:
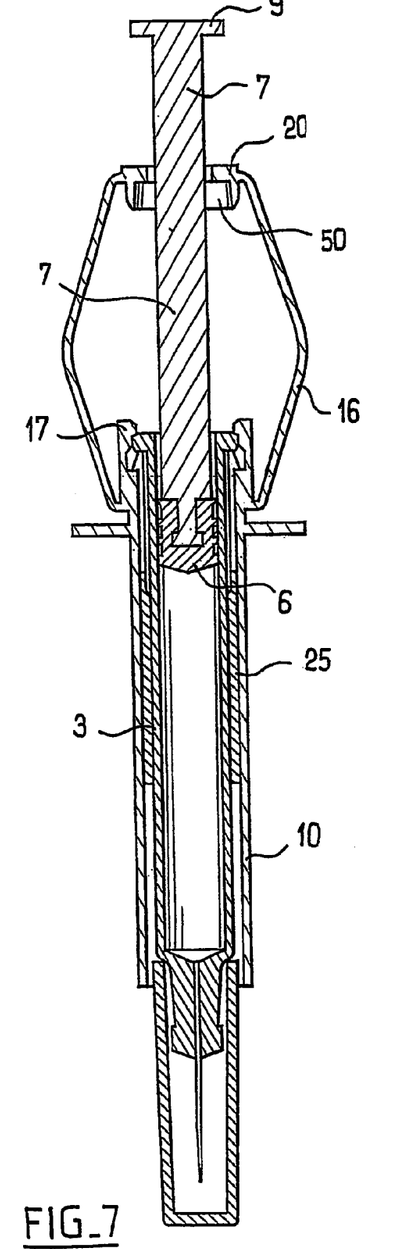
FIG. 7 is a diagrammatic and fragmentary axial section view of a safety device constituting a second embodiment of the invention.

FIG. 7 shows a safety device that is substantially analogous to the device 1, but that does not include bridges of material 18, having an annular rib 50 connected to the bottom of the ring 20. When the piston 6 is in the end-of-stroke position, this annular rib 50 comes to press against the tabs 17 and causes them to be moved apart so that they no longer retain the syringe body 3 in the protective sheath 10.

Figure 8:
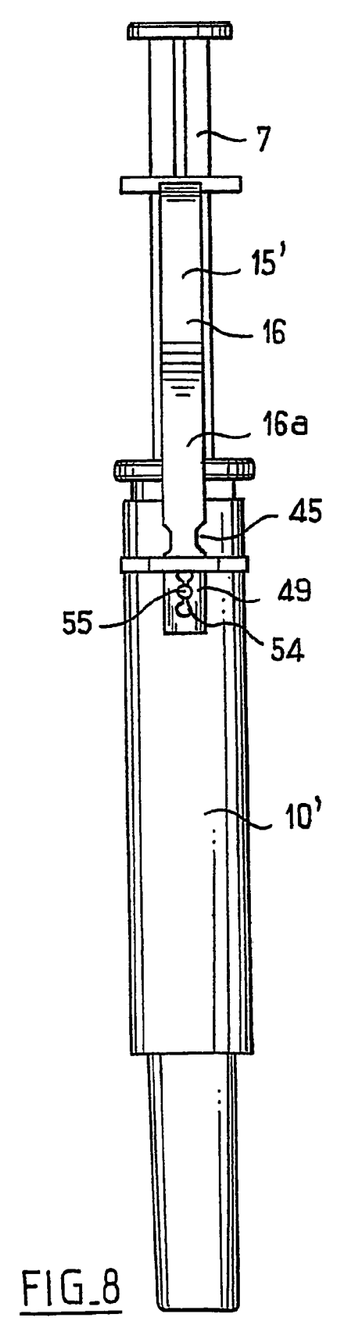
FIG. 8 is a diagrammatic side view of a safety device constituting a third embodiment of the invention.
Figure 9:
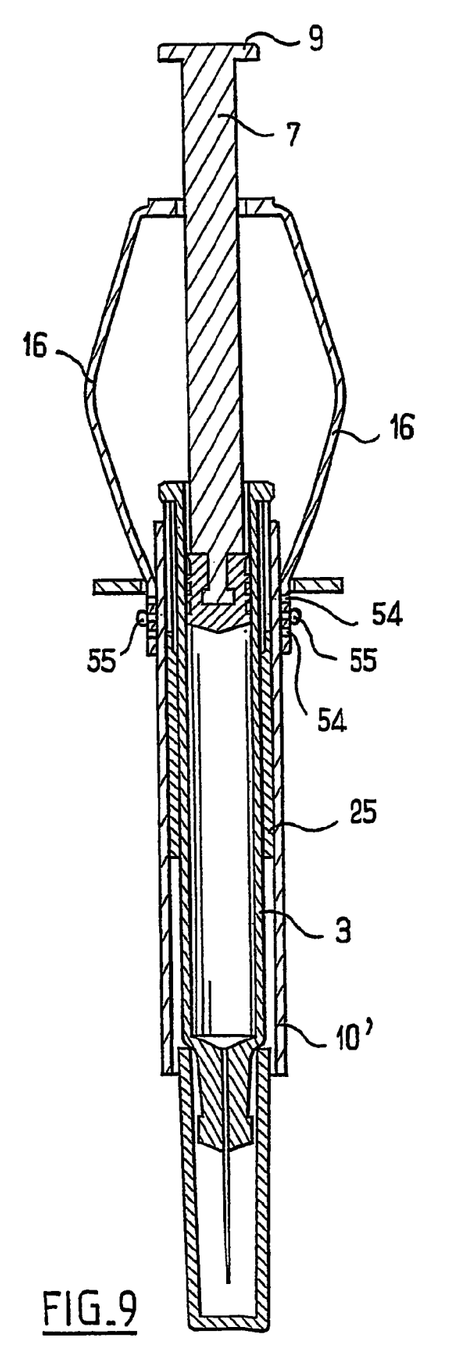
FIG. 9 is a diagrammatic axial section of IX—IX of the FIG. 8 device.

FIGS. 8 and 9 show a safety device constituting another embodiment of the invention. As can be seen in FIG. 8, this safety device comprises a resilient element 15' that differs from above-described resilient element 15 by the fact that it is constituted by a fitted element. The bottom branches 16a of the arms 16 are extended by respective straps 49 each pieced by a plurality of holes disposed in a longitudinal direction along the corresponding arm 16.

The protective sheath 10' has portions in relief forming studs 55 that are diametrically opposite, and each suitable for co-operating with a respective orifice 54 selected from amongst the orifices of an arm 16 as a function of the height desired for the resilient element 15'.

Figure 10:
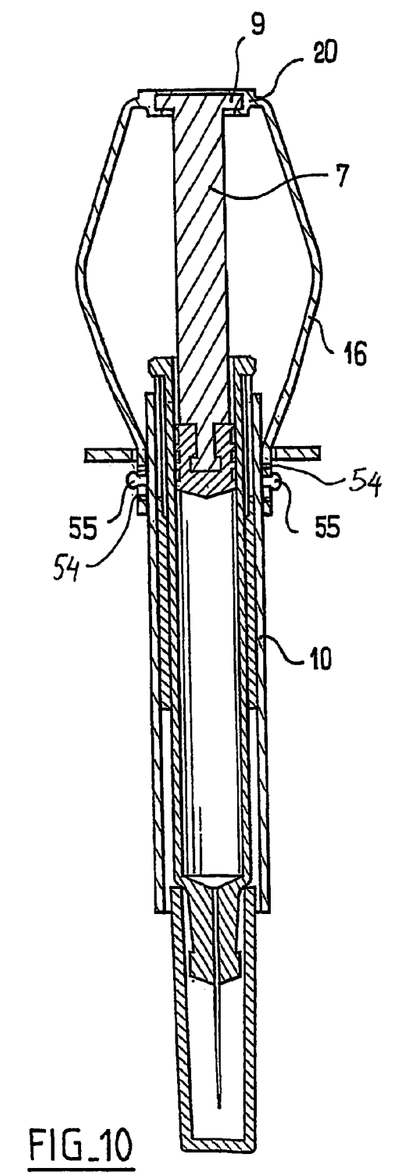
FIG. 10 is a diagrammatic and fragmentary axial section view of a safety device constituting a first embodiment of the invention.

FIG. 10 shows a safety device substantially analogous to that described with reference to FIGS. 8 and 9 but differing therefrom by the fact that the pusher 9 is secured to the ring 20 by the pusher 9 being snap-fastened in a groove of the ring 20. The height of the resilient element 15 is then adjusted by selecting suitable orifices 54 in which the portions in relief 55 are engaged.

Naturally, the invention is not limited to the embodiments described above.

In particular, a piston rod 7 can be provided that already includes the elastically-deformable arms 16, which are connected directly to the pusher 9.

The safety device may also include portions in relief enabling the syringe to be prevented from turning relative to the protective sheath.

The sheath may also include openings enabling the assembly constituted by the syringe and the sleeve to be grasped by a user.

What is claimed is:

1. A safety device for a prefilled syringe, the syringe comprising a body, a needle carrier at one end of the body, a piston movable inside the body, and a piston rod projecting beyond the body at its end opposite from the needle carrier and suitable for pushing the piston inside the body towards the needle carrier, said device comprising a protective sheath in which the syringe body can slide between an injection position in which the syringe needle extends outside the protective sheath, and a safe position in which the needle is withdrawn inside the protective sheath, the device further comprising a resilient element suitable for acting on the syringe during the sliding of the body of the syringe inside the sheath from its injection position towards its safe position to bring the body into its safe position after injection, said resilient element having two axial ends and at least two elastically-deformable arms, each of the arms having a first axial end and a second axial end, the first axial end of each of the arms being designed to cooperate with the piston rod and being arranged in such a manner as to be capable of sliding freely along the piston rod prior to injection, the second axial end of each of the arms being arranged so as to be capable of being fixed to the protective sheath.

2. A device according to claim 1, wherein each of the elastically-deformable arms is defined by a strip of material made for example of PP, SBS, EBS, PA, POM, or PE, there preferably being two such arms disposed facing each other.

3. A device according to claim 2, wherein each of said arms is generally V-shaped, with its concave sides facing inwards.

4. A device according to claim 3, wherein the branches of the V-shape of each of the arms are of different lengths.

5. A device according to claim 2, wherein the arms present local reductions in width.

6. A device according to claim 1, wherein the resilient element is made integrally with the protective sheath.

7. A device according to claim 6, wherein one of the ends of the resilient element is connected to the protective sheath and the other end is put into place on the piston rod, being free to slide relative thereto prior to injection.

8. A device according to claim 6, wherein the resilient element includes an annular split ring at one of its axial ends, which ring is suitable for engaging on the piston rod and is capable of sliding relative thereto.

9. A device according to claim 1, wherein the resilient element is constituted by a separate element suitable for being fitted to the protective sheath.

10. A device according to claim 9, wherein the resilient element includes fixing straps each pierced by a plurality of orifices in a longitudinal direction of the strap, and the protective sheath includes portions in relief each associated with one of the straps, each portion in relief being suitable for being fixed in one of the orifices of the associated strap.

11. A device according to claim 10, wherein the end of the resilient element remote from the strap is secured to the piston rod.

12. A device according to claim 1, including a holding element suitable for being deformed from a position for holding the syringe body in the sheath to a disengaged position enabling the syringe body to slide freely relative to the sheath.

13. A device according to claim 12, wherein the holding element comprises elastically-deformable tabs suitable for being splayed apart in order to take up the disengaged position.

14. A device according to claim 13, wherein the resilient element comprises bridges of material connecting the elastically-deformable arms to said elastically-deformable tabs in such a manner that, when the resilient element is subjected to compression, said bridges of material tend to move the tabs apart.

15. A device according to claim 13, wherein the resilient element comprises an annular rib arranged to bear against said tabs and move them apart when the resilient element is subjected to compression.

16. A device according to claim 1, including a locking element suitable for being fixed on the syringe body and arranged to retain it in its safe position, after injection.

17. A device according to claim 16, wherein said locking element comprises teeth suitable for coming into abutment against a top edge of the protective sheath when the syringe body is in its safe position.

18. A device according to claim 1, wherein the second axial end of each of the arms is arranged so as to be capable of being fixed to the protective sheath in a position of adjustable height.

19. A safety device for a prefilled syringe, the syringe comprising a body, a needle carrier at one end of the body, a piston movable inside the body, and a piston rod projecting beyond the body at its end opposite from the needle carrier and suitable for pushing the piston inside the body towards the needle carrier, said device comprising a protective sheath in which the syringe body can slide between an injection position in which the syringe needle extends outside the protective sheath, and a safe position in which the needle is withdrawn inside the protective sheath, the device further comprising a resilient element suitable for acting on the syringe to bring it into its safe position after injection, said resilient element having two axial ends and at least two elastically-deformable arms extending between said two axial ends, one of the ends being arranged in such a manner as to be capable of sliding freely along the piston rod prior to injection, and/or one of the ends being arranged so as to be capable of being fixed to the protective sheath in a position of adjustable height, wherein the resilient element is constituted by a separate element suitable for being fitted to the protective sheath and includes fixing straps each pierced by a plurality of orifices in a longitudinal direction of the strap, the protective sheath includes portions in relief each associated with one of the straps, each portion in relief being suitable for being fixed in one of the orifices of the associated strap.

20. A device according to claim 19, wherein the end of the resilient element remote from the strap is secured to the piston rod.

21. A safety device for a prefilled syringe, the syringe comprising a body, a needle carrier at one end of the body, a piston movable inside the body, and a piston rod projecting beyond the body at its end opposite from the needle carrier and suitable for pushing the piston inside the body towards the needle carrier, said device comprising a protective sheath in which the syringe body can slide between an injection position in which the syringe needle extends outside the protective sheath, and a safe position in which the needle is withdrawn inside the protective sheath, the device further comprising a resilient element suitable for acting on the syringe to bring it into its safe position after injection, said resilient element having two axial ends and at least two elastically-deformable arms extending between said two axial ends, one of the ends being arranged in such a manner as to be capable of sliding freely along the piston rod prior to injection, and/or one of the ends being arranged so as to be capable of being fixed to the protective sheath in a position of adjustable height, and a holding element suitable for being deformed from a position for holding the syringe body in the sheath to a disengaged position enabling the syringe body to slide freely relative to the sheath, wherein the holding element comprises elastically-deformable tabs suitable for being splayed apart in order to take up the disengaged position, and the resilient element comprises bridges of material connecting the elastically-deformable arms to said elastically-deformable tabs in such a manner that, when the resilient element is subjected to compression, said bridges of material tend to move the tabs apart.

22. A safety device for a prefilled syringe, the syringe comprising a body, a needle carrier at one end of the body, a piston movable inside the body, and a piston rod projecting beyond the body at its end opposite from the needle carrier and suitable for pushing the piston inside the body towards the needle carrier, said device comprising a protective sheath in which the syringe body can slide between an injection position in which the syringe needle extends outside the protective sheath, and a safe position in which the needle is withdrawn inside the protective sheath, the device comprising a resilient element suitable for acting on the syringe to bring in into its safe position after injection, said resilient element having two axial ends and at least two elastically-deformable arms extending between said two axial ends, one of the ends being arranged in such a manner as to be capable of sliding freely along the piston rod prior to injection, and/or one of the ends being arranged so as to be capable of being fixed to the protective sheath in a position of adjustable height, and a holding element suitable for being deformed from a position for holding the syringe body in the sheath to a disengaged position enabling the syringe body to slide freely relative to the sheath, wherein the holding element comprises elastically-deformable tabs suitable for being splayed apart in order to take up the disengaged position, and the resilient element comprises an annular rib arranged to bear against said tabs and move them apart when the resilient element is subjected to compression.

* * * * *